United States Patent [19]
Winkler

[11] 3,967,129
[45] June 29, 1976

[54] RADIATION SHIELDING CURTAIN

[75] Inventor: Norlin T. Winkler, Rochester, Minn.

[73] Assignee: Research Corporation, New York, N.Y.

[22] Filed: Apr. 28, 1075

[21] Appl. No.: 571,931

[52] U.S. Cl. .............................. 250/517; 160/332; 250/510; 250/519
[51] Int. Cl.² ...................... G21B 3/02; G21B 3/04
[58] Field of Search .......... 250/510, 515, 517, 519; 160/332

[56] References Cited
UNITED STATES PATENTS

| | | | |
|---|---|---|---|
| 1,634,312 | 7/1927 | Zecchino | 160/332 |
| 2,884,054 | 4/1959 | Bryant | 160/332 |
| 3,256,442 | 6/1966 | Sedlak | 250/519 |
| 3,622,432 | 11/1971 | McCluer | 250/519 |

FOREIGN PATENTS OR APPLICATIONS

| | | | |
|---|---|---|---|
| 766,886 | 1/1957 | United Kingdom | 250/519 |

*Primary Examiner*—Harold A. Dixon
*Attorney, Agent, or Firm*—Cooper, Dunham, Clark, Griffin & Moran

[57] ABSTRACT

A radiation shield in the form of a stranded curtain made up of bead-chains whose material and geometry are selected to produce a cross-sectional density that is the equivalent of 0.25 mm or more of lead and which curtain may be mounted on various radiological devices to shield against scattered radiation while offering a minimum of obstruction to the radiologist.

12 Claims, 5 Drawing Figures

RADIATION SHIELDING CURTAIN

BACKGROUND OF THE INVENTION

The present invention relates to radiation shielding devices and more particularly to a flexible stranded curtain of radiation-inhibiting material for use with radiological and fluoroscopic equipment.

The radiation levels to which busy radiologists are exposed during fluoroscopy may frequently exceed the maximum permissible dose of 5 rads per year for radiation workers as defined by the National Council on Radiation Protection and Measurement. While particular shielding devices, such as the lead apron worn during fluoroscopy, can reduce the actual dose to the body trunk and thighs to acceptable levels, other body organs particularly sensitive to radiation, such as the lens of the eye, are generally unshielded. During fluoroscopy a large portion of the scattered radiation to which the fluoroscopist is exposed is scattered from the patient and exits through the space between the fluoroscopic table top and the bottom of the image intensifier carriage. Although it has been recommended that for good practice flaps of 0.25 mm lead equivalence should be utilized on fluoroscopic equipment to close this space, and some fluoroscopic tables are equipped with collapsible or folding barriers, still the commercially available fluoroflaps and collapsible barriers tend to impede the fluoroscopist's activities. In addition, the problem may be complicated in certain applications by the need to maintain a sterile field in which instances conventional lead rubber or vinyl fluoroflaps are totally unsuitable.

The present invention accordingly provides a radiation shielding means which offers a minimum of obstruction to the radiologist, which is much more durable than the prior art devices and which can be readily sterilized for use during special procedures.

SUMMARY OF THE INVENTION

The present invention involves a method and means for shielding against stray radiation which comprises the constructing of a flexible radiation barrier by arranging a number of flexible strings of radiation shielding material adjacent to each other to form a stranded curtain having a depth which is the equivalent of 0.25 mm of lead. The strings may be of bead-chain or other arrays of pliantly joined elements and are connected by suitable means at their upper ends to form one or more layers, the number being determined by the density of the material used and the porosity of each layer as a result of the shape of the elements. The curtain thus produced allows the radiologist greater freedom of action in permitting him, for example, to thrust his hand through it at any point whereupon the curtain will part and drape itself around his wrist without interference with his hand or arm movements while still affording the necessary protection. This curtain can be sterilized, is durable, and can be adapted to provide up to a twenty-fold reduction in radiation exposure to critical organs such as the lens of the eye.

DETAILED DESCRIPTION OF A PREFERRED EMBODIMENT

It should initially be noted that it is the practice of the art in constructing radiation shields that the material and the geometry be selected to absorb or block radiation to an extent which is equivalent to the radiation blocking ability of a predetermined thickness of solid lead. It will accordingly be appreciated that the basic radiation shielding elements used in the construction of the present invention may be made of various materials or combination of materials, and with varying geometries, all of which combinations and variations will be within the purview of one skilled in the art, having the benefit of the teaching of the present invention.

The essential component of the present invention is a radiation-shielding element which may be elongated to form a strand-like member but which, preferably, is flexibly connected to a number of other similar elements to form a pliant or flexible string. The individual elements may be in the form of spheres, cylinders, strips, cubes, ellipsoids, triangles, or the like, and they may be solid, jacketed, layered or fluid-containing, or any combinations of the foregoing, in order to achieve the proper density and geometry necessary for the desired lead equivalence. For the purposes of the description the elementary string will be in the form of a spherical-bead chain.

Figure 1:
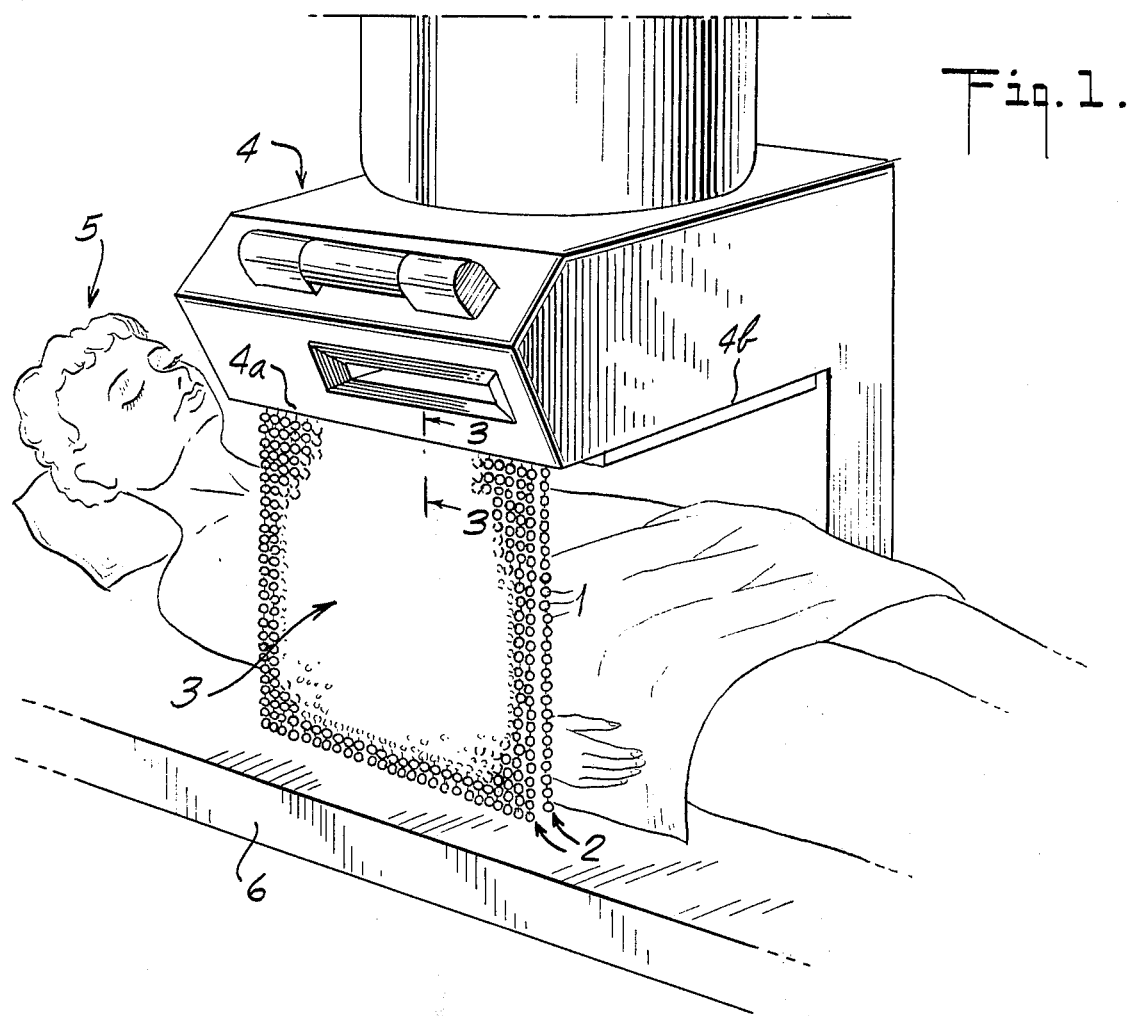
FIG. 1 is a perspective view of a patient undergoing a fluoroscopic examination using a fluoroscopic unit equipped with a radiation shielding curtain in accordance with the present invention.

In accordance with the invention and as shown in FIG. 1, a number of spherical-bead elements 1 connected in strings or chains 2 are assembled to form a stranded curtain 3, having one or more layers which may be mounted on appropriate radiological apparatus in a suitable position to achieve the requisite radiation shielding. The particular embodiment shown in FIG. 1 has a plurality of bead-chain strings 2 arranged as a double-layer bead-chain curtain 3 which is mounted on a fluoroscopic unit 4, in a position adjacent a horizontally disposed patient 5, for blocking the radiation scattered from the patient in the space between the fluoroscopic tabletop 6 and one bottom edge 4a of the image intensifier carriage of unit 4. It will be seen that with a vertically oriented patient, the curtain may be hung from the other edge 4b of the fluoroscopic unit to shield against the scattered radiation.

Figure 2:
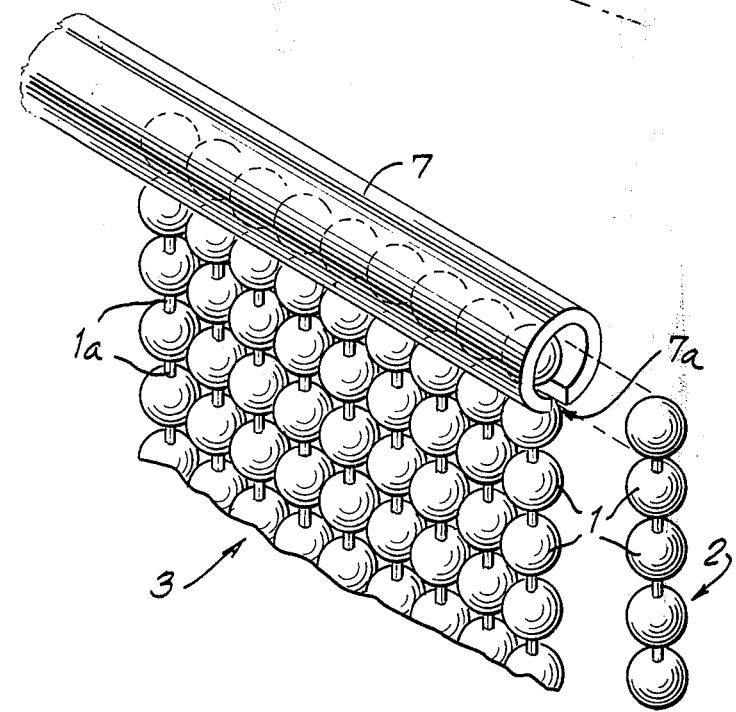
FIG. 2 is a perspective view illustrating the construction of the radiation-inhibiting elements and the means for mounting them in the form of a curtain in one embodiment of the present invention.

As shown in FIG. 2 to form the bead-chain strings 2 into a curtain 3, it is preferred to use a mounting means in the form of a hollow pipe or tube 7 such as of brass with an inside diameter sufficient to accommodate a bead 1 therein. The pipe 7 may be cut to the desired length and a slot 7a milled along its length of sufficient size to accommodate the short segment of wire 1a between the beads 1. Each string of bead-chain 2 may then be strung onto the pipe 7 by inserting the uppermost bead in the hollow interior of the pipe with the wire segment 1a disposed in the milled slot 7a and successively sliding each string along the pipe into abutment with the previous string until the full length of the pipe is filled. The beads may be held within the pipe at the far end by halting the milled slot before it extends the full length of the pipe. Alternatively, both ends of the pipe interior may be sealed by soldering or crimping the ends shut holding the beads on the upper end of each string abuttingly in place and accordingly forming a single-layer curtain of bead chain.

Figure 3:
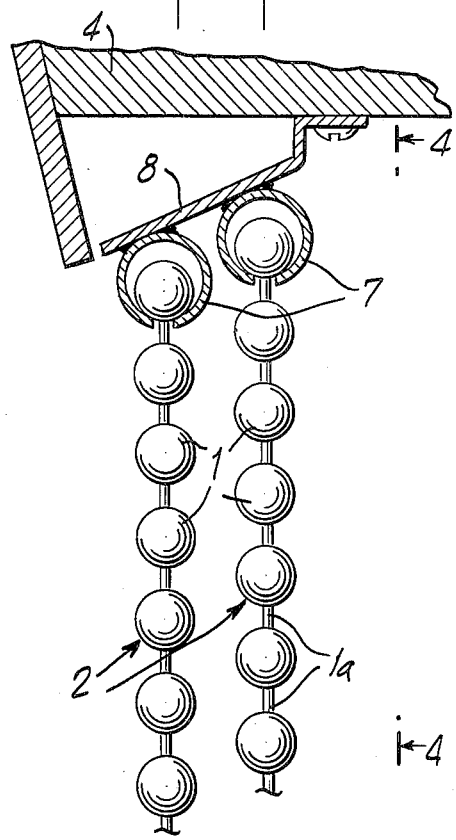
FIG. 3 is a sectional view illustrating an arrangement for mounting the curtain of FIG. 2 on an apparatus such as shown in FIG. 1 taken along the lines 3—3.
Figure 4:
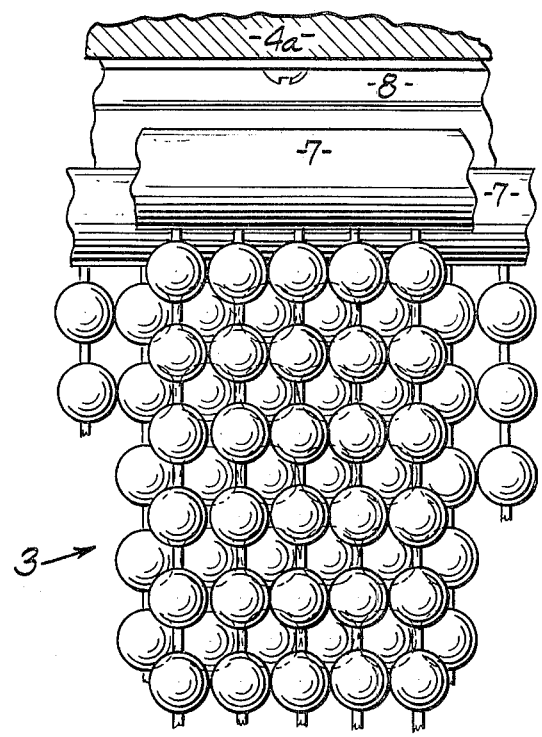
FIG. 4 is a view in elevation taken along the lines 4—4 in FIG. 3.

Although a single-layer curtain may suffice if the bead elements are of a material of considerable size and density, it is ordinarily preferred in order to maximize its pliancy or flexibility, that two or more layers of bead chain be used for the protective curtain. Accordingly, the mounting pipes 7 for each layer may be soldered adjacent to each other to a suitable mounting bracket 8 such as shown in FIG. 3. It is preferred, for example in a two-layer curtain, that the bracket 8 be formed such that the back layer of the curtain is shifted slightly laterally and vertically to cause the beads in the back row to close the spaces or interstices between the beads in the front row. So arranged, the beads present a substantially solid curtain to impinging radiation as illustrated in FIG. 4.

It is also contemplated to use various other forms of mounting means, such as pipes of flexible material (e.g. brass, copper tubing, or plastics) for holding the uppermost elements or beads of the chains, each particularly adapted to facilitate the mounting of the curtains on diverse radiological equipment and in various locations.

It will be seen that this method of construction is readily adaptable for making curtains of any desired length and width as may be called for in various diverse installations. A particular embodiment found suitable for installation in gastro-intestinal fluoroscopic equipment is 15 inches wide by 10 inches long and constructed of 0.25 inch, short centered, nickel-plated brass bead chain. Suitable bead chain for this purpose is commercially obtainable from the Bead Chain Manufacturing Company, Bridgeport, Connecticut 06604, as their product No. 13-S(5).

Figure 5:
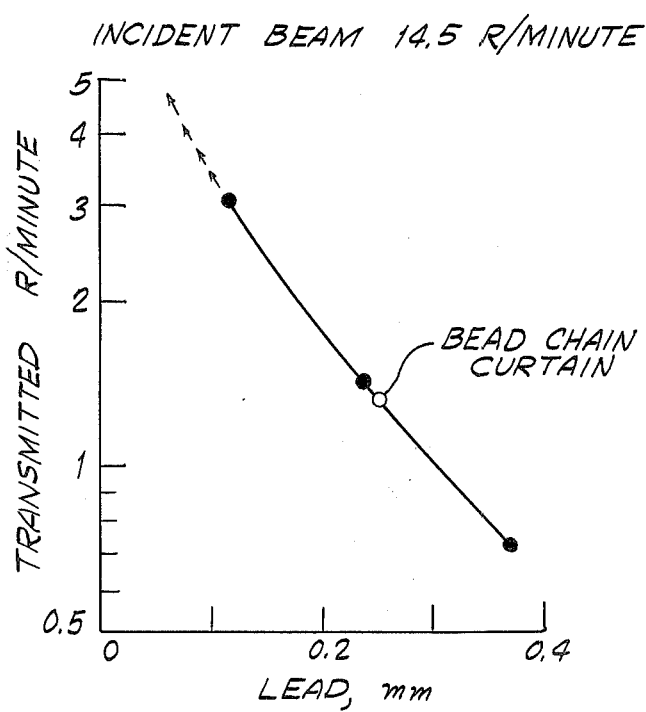
FIG. 5 is a plot of measurements made to determine the radiation blocking power of a curtain in accordance with the present invention as compared to that of a solid lead plate.

A curtain of the above-described construction has been tested to determine its lead equivalence. Measurements were made using a single-phase diagnostic X-ray unit as an X-ray source. The unit was operated at 100 kv.p. with a conventional added filter of 2 mm of aluminum. Thus, measured lead equivalence was determined for an X-ray beam quality typical for practical use conditions. A Victoreen Radocon ratemeter with a No. 601 probe was used as a measuring instrument. Various thicknesses of lead were used and measurements of X-ray transmission plotted. Transmission measurements through a double-layer, bead chain curtain of the above type were compared to the transmission measurements through lead to determine lead equivalence. The double-layer bead chain curtain was found to be equivalent to 0.24 mm of lead under the described conditions as indicated in the plot in FIG. 5.

To further determine the scattered radiation protection provided by such a bead chain curtain under actual fluoroscopic conditions, an Alderson whole body phantom was placed on the fluoroscopic table 4 and fluoroscoped as if it were the patient 5 shown in FIG. 1. Scattered radiation measurements were made with and without the bead chain curtain. Fluoroscopic exposure factors were maximum for the equipment, 2.5 ma., 125 kv.p. These fluoroscopic factors resulted in a 9.0 roentgen-per-minute entrance exposure to the phantom. Radiation field size was such that images of the fluoroscopic shutters were just visible on a TV monitor as a 9 inch image system. The radiation field was entirely contained within the phanton and centered to the right middle quadrant of the abdomen to duplicate the worst scattered radiation conditions existing for fluoroscopy of the colon and the duodenum when patients are examined. Measurements were taken and tabulated with the phantom disposed in the horizontal and vertical positions. Up to a twenty-fold reduction in scattered radiation exposure was found with the use of the bead-chain protective curtain, as indicated in the following tabulated results.

TABLE I

SCATTERED RADIATION MEASUREMENTS MADE WITH AND WITHOUT BEAD CHAIN

Fluoroscopic Table Horizontal (Colon fluoroscopy, fluoroscopist at side of table)

| | Without Bead Chain | With Bead Chain | Protection Ratio ($I_e/I_t$) |
|---|---|---|---|
| Fluoroscopist's waist level | 2,600 mr./hr. | 180 mr./hr. | 14.5:1.0 |
| Level of sternal notch | 400 mr./hr. | 20 mr./hr. | 20:1.0 |
| Eye level | 200 mr./hr. | 10 mr./hr. | 20:1.0 |

Fluoroscopic Table Vertical (Upper GI, fluoroscopist facing upright table)

| | Without Bead Chain | With Bead Chain | Protection Ratio |
|---|---|---|---|
| Fluoroscopist's waist level | 80 mr./hr. | 5–10 mr./hr. | 12–20:1.0 |
| Level of sternal notch | 50 mr./hr. | 5–10 mr./hr. | 5–10:1.0 |
| Eye Level | 5–10 mr./hr.* | 5–10 mr./hr. | 1.0–:1.0 |

It should be noted in connection with the last tabulation that with the patient in the vertical position a great deal of shielding from scattered radiation is provided by the image amplifier and its supporting structure.

The curtain of the present invention particularly lends itself to sterilization since unlike most prior art devices it can be exposed to high temperatures, such as 275° F in an autoclave, without deteriorating in any way, and is extremely durable as it will not break or tear with continued use as is the case with existing lead rubber or vinyl flaps.

In conclusion it should be noted that the preferred cross-sectional density of a curtain in accordance with the present invention has been cited throughout the description as being the equivalent of 0.25 mm of lead, which is the present acceptable minimum standard for shielding of the National Council on Radiation Protection and Measurement. This numerical value is not meant to be critical in itself to the invention, but rather is intended to represent the minimum standard set at any time by the Council or found to be acceptable in the art.

I claim:

1. A method of constructing a radiation shield comprising the steps of:
    assembling a plurality of radiation-shielding elements;
    connecting said elements in sets to form a plurality of elongated strings of said elements;
    disposing the upper ends of said strings adjacent to each other to form a stranded curtain; and
    selecting the material and geometry of said elements such that said curtain has a cross-section density which is the equivalent of a predetermined thickness of lead.

2. A method as in claim 1 wherein said upper ends are disposed in two parallel rows to form a double-layer curtain.

3. A method as in claim 2 wherein said elongated strings of said elements comprise strands of bead chain and the beads in one layer of said curtain are disposed opposite the interstices in the adjoining layer.

4. A method as in claim 1 wherein said predetermined thickness of lead is at least 0.25 mm.

5. A method as in claim 1 wherein the material and geometry of said radiation shielding elements comprise spherical metal beads.

6. A radiation shield comprising:
    a plurality of flexible strings of radiation-shielding material; and
    means for holding the upper ends of said strings adjacent to each other to form a flexible stranded curtain having a cross-sectional density which is the equivalent of at least 0.25 mm of lead.

7. A shield as in claim 6 wherein each of said strings comprises:
    a plurality of radiation-shielding elements; and
    means for connecting said elements in a set to form a flexible chain.

8. A shield as in claim 7 wherein said holding means comprises
    a first tubular means for accommodating at least one of said radiation-shielding elements and having a longitudinal slot therein for accommodating at least one of said connecting means.

9. A shield as in claim 8 wherein said holding means further comprises a second tubular means for accommodating at least one of said radiation-shielding elements and disposed adjacent to said first tubular means such that the chains held by each form a double-layer stranded curtain.

10. A shield as in claim 9 wherein said holding means further comprises means for offsetting said first tubular means from said second tubular means such that the radiation-shielding elements in said first bead chain are disposed opposite the interstices in said second bead chain.

11. A shield as in claim 6 wherein said radiation-shielding elements comprise spherical beads.

12. A shield as in claim 6 wherein said flexible strings comprise 0.25 inch, short-centered, nickel-plated brass bead chain.

* * * * *